(12) United States Patent
Kamal et al.

(10) Patent No.: US 6,884,799 B2
(45) Date of Patent: Apr. 26, 2005

(54) NON-CROSS-LINKING PYRROLO[2,1-C][1,4] BENZODIAZEPINES AND PROCESS THEREOF

(75) Inventors: Ahmed Kamal, Hyderabad (IN);
Gujjar Ramesh, Hyderabad (IN);
Olepu Srinivas, Hyderabad (IN);
Poddutoori Ramulu, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/401,782

(22) Filed: Mar. 31, 2003

(65) Prior Publication Data

US 2004/0192679 A1 Sep. 30, 2004

(51) Int. Cl.$^7$ .................. C07D 487/00; A61K 31/55
(52) U.S. Cl. ........................... 514/220; 540/96
(58) Field of Search .................... 514/220; 540/496

(56) References Cited

U.S. PATENT DOCUMENTS 6,362,331 B1 * 3/2002 Kamal et al. .............. 540/497

FOREIGN PATENT DOCUMENTS

WO    WO 93/18045    * 9/1993

OTHER PUBLICATIONS

A. Kamal et al., "Design, Synthesis, and Evaluation of New Noncross–Linking Pyrrolobenzodiazepine Dimers with Efficient DNA Binding Ability and Potent Antitumor Activity", J. Med. Chem. 2002, 45, 4679–4688.

D. Thurston et al., "Synthesis of Sequence–Selective C8–Linked Pyrrolo[2,1–c] [1,4]benzodiazepine DNA Interstrand Cross–Linking Agents", J. Org. Chem., 1996, 61, 8141–8147.

* cited by examiner

Primary Examiner—Bruck Kifle
(74) Attorney, Agent, or Firm—Birch, Stewart, Kolasch & Birch, LLP (57) ABSTRACT

The present invention relates to novel pyrrolo[2,1-c][1,4] benzodiazepines compounds of general formula V as shown below, which are useful as potential antitumour agents and a process of preparing these compounds; particularly the present invention provides a process for the preparation of 7-methoxy-8-{n-[7-methoxy-(11aS)-1,2,3,10,11,11a-hexahydro-5H-pyrrolo[2,1-c][1,4]ben-zodiazepine-5-one-8-yloxy]alkyloxy}-(11aS)-1,2,3,11a-tetrahydro-5H-pyrrolo[2,1-c][1,4]benzodiazepin-5-one, with varying aliphatic chain length and its 2-hydroxy derivatives.

V

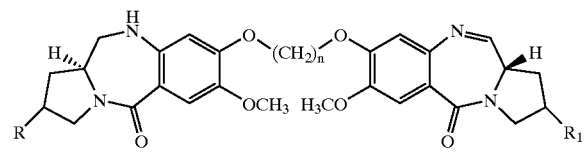

18 Claims, 1 Drawing Sheet

Figure 1

NON-CROSS-LINKING PYRROLO[2,1-C][1,4] BENZODIAZEPINES AND PROCESS THEREOF

FILED OF THE INVENTION

The present invention provides novel pyrrolo[2,1-c][1,4] benzodiazepines which are useful as potential antitumour agents. This invention relates to a process for the preparation of new pyrrolo[2,1-c][1,4]benzodiazepines compounds useful as antitumour agents. More particularly, it provides a process for the preparation of 7-methoxy-8-{n-[7-methoxy-(11aS)-1,2,3,10,11,11a-hexahydro-5H-pyrrolo[2,1-c][1,4]ben-zodiazepine-5-one-8-yloxy]alkyloxy}-(11aS)-1,2,3,11a-tetrahydro-5H-pyrrolo[2,1-c][1,4]benzodiazepin-5-one, with aliphatic chain length variation compounds and its 2-hydroxy derivatives having anticancer (antitumour) activity. The structural formula of novel pyrrolo[2,1-c][1,4] benzodiazepine is as follows.

V where R and $R_1$ is H and/or OH; and n is 3 to 5

BACKGROUND AND PRIOR ART REFERENCES

In the last few years, a growing interest has been shown in the development of new pyrrolo[2,1-c][1,4] benzodiazepines (PBDs). These antibiotics react covalently with DNA to form an N2-guanine adduct that lies within the minor groove of duplex DNA via an acid-labile aminal bond to the electrophilic imine at the N10-C11 position. (Ref. Kunimoto, S.; Masuda, T.; Kanbayashi, N.; Hamada, M.; Naganawa, H.; Miyamoto, M.; Takeuchi, T. and Unezawa, H. *J. Antibiot.* 1980, 33, 665.; Kohn, K. W. and Speous, C. L. *J. Mol. Biol.* 1970, 51, 551.; Hurley, L. H.; Gairpla, C. and Zmijewski, M. *Biochem. Biophys. Act.* 1977, 475, 521.; Kaplan, D. J. and Hurley, L. H. *Biochmestry* 1981, 20, 7572). The molecules have a right-handed twist which allows them to follow the curvature of the minor groove of B-form double-stranded DNA spanning three base pairs. A recent development has been the linking of two PBD units through their C 8 positions to give bisfunctional alkylating agents capable of cross-linking DNA (Ref: Thurston, D. E.; Bose, D. S.; Thomson, A. S.; Howard, P. W.; Leoni, A.; Croker, S. J.; Jenkins, T. C.; Neidle, S. and Hurley, L. H. *J. Org. Chem.* 1996, 61, 8141–8147). Recently, a non-cross-linking mixed imine-amide PBD dimers have been synthesized that have significant DNA binding ability and potent anti tumour activitiy (Kamal, A.; Laxman, N.; Ramesh, G.; Ramulu, P and Srinivas, O. U.S. Pat. No. 636,233. dt 26-Mar.-2002.; Kamal, A.; Ramesh, G.; Laxman, N.; Ramulu, P.; Srinivas, O.; Neelima, K.; Kondapi, A. K.; Srinu, V. B.; Nagarajaram, H. M. *J. Med. Chem.* 2002, 45, 4679).

Naturally occurring pyrrolo[2,1-c][1,4]benzodiazepines belongs to a group of antitumour antibiotics derived from *Streptomyces* species. Recently, there is much anthramycin

DC-81

DC-81 dimers (n = 3–5); DSB-120 (n = 3)

impetus for the PBD systems as they can recognize and bind to specific sequence of DNA. Examples of naturally occurring PBD's include anthramycin, DC-81, tomaymycin, sibiromycin and neothramycin.

However, the clinical efficacy for these antibiotics is hindered by several limitations, such as poor water solubility, cardiotoxicity and metabolic inactivation.

The compounds of present invention has a difference with C-8 linked secondary amine congeners by the replacement of phenolic hydrogen of (11aS)-8-Hydroxy-7-methoxy-1,2,3,11a-tetrahydro-5H-pyrrolo[2,1-c][1,4]benzodiazepine-5-one (DC-81).

Pyrrolo[2,1-c][1,4]benzodiazepine-5-ones are a class of compounds that bind to DNA by non-covalent interactions such as hydrophobic, Vanderwaal's interactions and hydrogen bonding between ring substituents and DNA, are also responsible for the influence on the sequence selectivity.

OBJECTS OF THE INVENTION

The main object of the present invention is to provide novel compound and its derivatives having anti-tumor activity i.e. Anti-cancer activities Another object of the present invention is to provide new pyrrolo[2,1-c][1,4]benzodiazepines useful as antitumour agents.

Another objective of the present invention is to provide a process for the preparation of novel pyrrolo[2,1-c][1,4] benzodiazepines useful as antitumour agents.

Another object of the invention is to provide process for the preparation of novel compounds.

Another object of the invention is to provide a pharmaceutical composition for the treatment of cancer and other tumors.

One more object of the invention is to provide a method of treating subjects suffering from cancer and related diseases.

SUMMARY OF THE INVENTION

Accordingly the present invention provides novel pyrrolo[2,1-c][1,4]benzodiazepine of formula V wherein R=H, OH, $R_1$=H, OH and n is 3 to 5 and a process thereof.

V

DETAILED DESCRIPTION OF THE INVENTION

Accordingly, the present invention provides pyrrolo[2,1-c][1,4]benzodiazepine compounds of general formula V, where R and $R_1$ is H and/or OH; and n is 3 to 5.

One embodiment of the invention provides pyrrolobenzodiazepine having structural formula shown below where R=$R_1$=H and n=3.

One embodiment of the invention provides pyrrolobenzodiazepine having structural formula shown below, where R=$R_1$=H and n=4.

One more embodiment of the invention provides pyrrolobenzodiazepine having structural formula shown below, where R=$R_1$=H and n=5.

Still another embodiment of the invention provides pyrrolobenzodiazepine having structural formula shown below where R=OH, $R_1$=H and n=3.

Another embodiment of the invention provides pyrrolobenzodiazepine having structural formula shown below, where R=OH, $R_1$=H and n=4.

Still another embodiment of the invention provides pyrrolobenzodiazepine having structural formula shown below, where R=OH, $R_1$=H and n=5.

In another embodiment, the invention provides a pyrrolobenzodiazepine compound having structural formula shown below, where R=H, $R_1$=OH and n=3.

In another embodiment, the invention provides a pyrrolobenzodiazepine compound having structural formula shown below, where R=H, $R_1$=OH and n=4.

In another embodiment, the invention provides a pyrrolobenzodiazepine compound having structural formula shown below, where R=H, $R_1$=OH and n=5.

Another embodiment of the invention relates to the activity of the pyrrolo[2,1-c][1,4]benzodiazepine of formula V against human tumor cell lines.

Still another embodiment of the invention provides growth inhibition activity of these compounds against various types of cancer cells like leukemia, non-small-cell lung, colon, CNS, melanoma, ovarian, prostate and breast cancer.

One more embodiment of the invention relates to a process for the preparation of compounds, the said process comprising steps of:

a) reacting a compound of formula (1) with formula (II) in presence of mild base in water miscible aprotic organic solvent at reflux temperature for a period of 16 h to 48 h, b) pouring the reaction mixture of step (a) into water, extracting with ethyl acetate separating organic layer and discarding aqueous layer, c) evaporating the organic layer of step (b) to obtain a residue which is purified to get compound of formula (III), d) reducing the nitro compound of formula (III) in halogenated solvent, adding stannous chloride dihydrate, refluxing for a period of 0.5 h to 2 h, e) adjusting the pH of the reaction mixture of step (d) to 8.0 using alkali bicarbonate solution, f) extracting the step (e) solution with ethylacetate, evaporating the ethylacetate extract under reduced pressure to obtain crude compound of formula (IV), g) providing a solution of compound of formula (IV) in a mixture of acetonitrile/$H_2O$ adding mercuric chloride, calcium carbonate, stirring at room temperature for 6 h to 12 h, h) filtering and evaporating the organic layer under reduced pressure to obtain a residue which is diluted with ethyl acetate, i) adding saturated solution of sodium bicarbonate to ethylacetate solution of step (h) at room temperature, j) filtering the solution of step (I) through celite bed, evaporating the filtrate to obtain a residue containing crude compound of formula V, and k) purifying crude compound of step (j) using silica gel as an adsorbent to obtain pure compound of formula (V) wherein R and $R_1$ are as defined earlier.

Still another embodiment, wherein the aprotic organic solvent used in step (a) is selected from a group consisting of tetrahydrofuran, acetone or dimethyl formamide.

Yet another embodiment, the mild base used in step (a) is selected from a group of sodium carbonate, potassium carbonate, lithium carbonate, barium carbonate and cesium carbonate.

Yet another embodiment, in step (d) the halogenated solvent used is selected from a group consisting of carbon tetra chloride, chloroform and dichloromethane, preferably dichloromethane.

Still another embodiment of the invention relates to the process, wherein in step (c) the alkali carbonate solution used is selected from a solution of sodium bicarbonate potassium bicarbonate or lithium bicarbonate.

One more embodiment of the invention provide pharmaceutical composition effective against human cancer cell lines, said composition comprising effective amount of compound pyrrolo[2,1-c][1,4]benzodiazepine of general formula V, where R and $R_1$ is H and/or OH; and n is 3 to 5, along with pharmaceutically acceptable additives.

The composition is administered to mammals including human beings. The composition is administered orally, systemically or by any other conventional methods. The pharmaceutically acceptable additives are selected from a group consisting of carriers, diluents, solvents, filler, lubricants, excipients, binders and stabilizers.

Another embodiment of the invention, the said composition inhibits the growth of cancer cells.

Still another embodiment, the said composition inhibits the growth of the cancer cells such as leukemia, non-small-cell lung, colon, CNS, melanoma, ovarian, prostate and breast cancer.

The present process provides a process for preparation of pyrrolo[2,1-c][1,4]benzodiazepines of formula V of the drawing accompanying the specification wherein R is H, OH, $R_1$ is H, OH and n is 3 to 5 which comprises: (2S)-N-[4-(n-bromoalkoxy)-5-methoxy-2-nitrobenzoyl] pyrrolidine-2-carboxaldehyde diethyl thioacetal wherein $R_1$ is H, OH and n is 3–5 compounds of formula I with secondary amine of formula II wherein R is H and OH in presence of an inorganic mild bases like $K_2CO_3$, $CsCO_3$ and $BaCO_3$ in presence of aprotic water miscible organic solvents like acetone, THF, and DMF upto refluxing temperature for a period upto 12–48 hours isolating (2S)-N-{4-[n-(7-methoxy-(11aS)-1,2,3,10,11,11a-hexahydro-5H-pyrrolo [2,1-c][1,4]benzodiazepine-5-one-8-yloxy)alkyloxy]-5-methoxy-2-nitrobenzoyl}-pyrrolidine-2-carboxaldehyde diethyl thioacetal and III wherein R is H, OH, $R_1$ is H, OH and n is 3 to 5 by conventional methods, reducing the above nitro compounds of formula III with $SnCl_2.2H_2O$ in presence of organic solvent up to a reflux temperature, isolating the (2S)-N-{4-[n-(7-methoxy-(11aS)-1,2,3,10,11,11a-hexahydro-5H-pyrrolo[2,1-c][1,4]benzodi-azepine-5-one-8-loxy)alkoxy]-5-methoxy-2-aminobenzoyl}pyrrolidine-2-carboxaldehyde diethyl thioacetal of formula IV wherein R is H, OH, $R_1$ is H, OH and n is 3 to 5 by known methods, reacting the above said amino compound of formula IV with known deprotecting agents in a conventional manner to give novel pyrrolo[2,1-c][1,4]benzodiazepines of formula V wherein R is H, OH, $R_1$ is H, OH and n is 3 to 5.

The precursors, (2S)-N-[4-(n-bromoalkoxy)-5-methoxy-2-nitrobenzoyl]pyrrolidine-2-carboxaldehyde diethyl thioacetal of formula I prepared by literature methods (Ref: Kamal, A.; Laxman, N.; Ramesh, G.; Nileema, K.; Kondapi, A. K. *Chem. Commun.* 2001, 437) and 8-Hydroxy 7-methoxy-(11aS)-1,2,3,10,11,11a-hexahydro-5H-pyrrolo [2,1-c][1,4]benzodiazepine-5-one of formula II prepared by literature method (Ref: Kamal, A.; Howard, P. W.; Reddy, B. S. N.; Reddy, B. S. P.; Thurston, D. E. *Tetrahedron* 1997, 53, 3223–3230).

Some representative compounds of formula V present invention are given below 1) 7-Methoxy-8-{3-[7-methoxy-(11aS)-1,2,3,10,11,11a-hexahydro-5H-pyrrolo[2,1-c][1,4]benzodiazepine-5-one-8-yloxy]propoxy}-(11aS)-1,2,3,11a-tetrahydro-5H-pyrrolo[2,1-c][1,4]benzodiazepine-5-one 2) 7-Methoxy-8-{4-[7-methoxy-(11aS)-1,2,3,10,11,11a-hexahydro-5H-pyrrolo[2,1-c][1,4]benzodiazepine-5-one-8-yloxy]butoxy}-(11aS)-1,2,3,11a-tetrahydro-5H-pyrrolo[2,1-c][1,4]benzodiazepine-5-one 3) 7-Methoxy-8-{5-[7-methoxy-(11aS)-1,2,3,10,11,11a-hexahydro-5H-pyrrolo[2,1-c][1,4]benzodiazepine-5-one-8-yloxy]pentyloxy}-(11aS)-1,2,3,11a-tetrahydro-5H-pyrrolo[2,1-c][1,4]benzodiazepine-5-one 4) 7-Methoxy-8-{3-[7-methoxy-(2R)-hydroxy-(11aS)-1,2,3,10,11,11a-hexahydro-5H-pyrrolo[2,1-c][1,4] benzodiazepine-5-one-8-yloxy]propoxy}-(11aS)-1,2,3,11a-tetrahydro-5H-pyrrolo[2,1-c][1,4]benzodiazepine-5-one 5) 7-Methoxy-8-{4-[7-methoxy-(2R)-hydroxy-(11aS)-1,2,3,10,11,11a-hexahydro-5H-pyrrolo[2,1-c][1,4] benzodiazepine-5-one-8-yloxy]butoxy}-(11aS)-1,2,3,11a-tetrahydro-5H-pyrrolo[2,1-c][1,4]benzodiazepine-5-one 6) 7-Methoxy-8-{5-[7-methoxy-(2R)-hydroxy-(11aS)-1,2,3,10,11,11a-hexahydro-5H-pyrrolo[2,1-c][1,4]benzodiazepine-5-one-8-yloxy]pentyloxy}-(11aS)-1,2,3,11a-tetrahydro-5H-pyrrolo[2,1-c][1,4]benzodiazepine-5-one 7) 7-Methoxy-8-{3-[7-methoxy-(11aS)-1,2,3,10,11,11a-hexahydro-5H-pyrrolo[2,1-c][1,4]benzodiazepine-5-one-8-yloxy]propoxy}-(2R)-hydroxy-(11aS)-1,2,3,11a-tetrahydro-5H-pyrrolo[2,1-c][1,4]benzodiazepine-5-one 8) 7-Methoxy-8-{4-[7-methoxy-(11aS)-1,2,3,10,11,11a-hexahydro-5H-pyrrolo[2,1-c][1,4]benzodiazepine-5-one-8-yloxy]butoxy}-(2R)-hydroxy-(11aS)-1,2,3,11a-tetrahydro-5H-pyrrolo[2,1-c][1,4]benzodiazepine-5-one 9) 7-Methoxy-8-{5-[7-methoxy-(11aS)-1,2,3,10,11,11a-hexahydro-5H-pyrrolo[2,1-c][1,4]benzodiazepine-5-one-8-yloxy]pentyloxy}-(2R)-hydroxy-(11aS)-1,2,3,11a-tetrahydro-5H-pyrrolo[2,1-c][1,4]benzodiazepine-5-one The process of preparation of new pyrrolo[2,1-c][1,4]benzodiazepines is disclosed and claimed in applicants co pending application Ser. No. 10/401,754.

Figure 1:
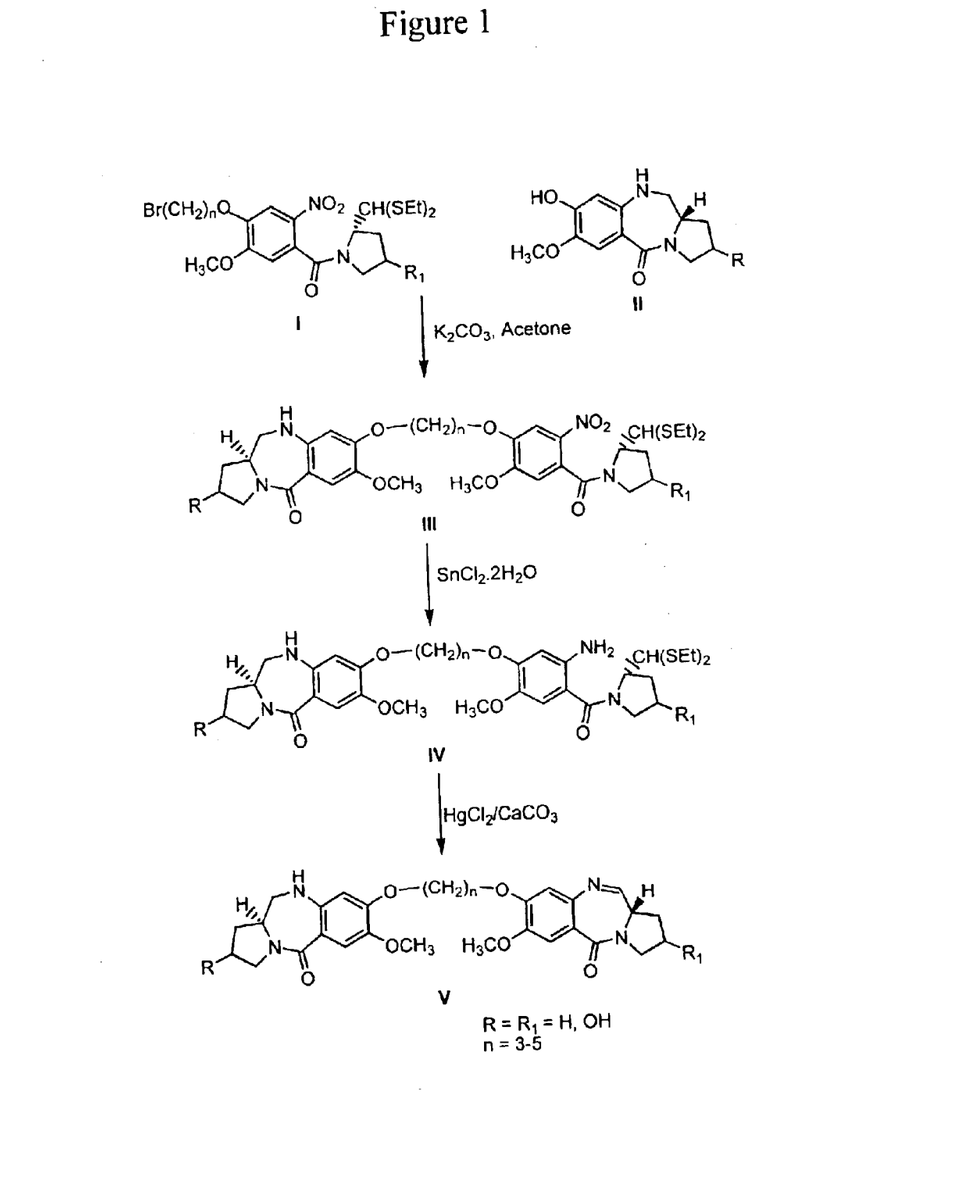
FIG. 1 represents schematic diagram of preparing compound of general formula V.

These new analogues of pyrrolo[2,1-c][1,4]benzodiazepines linked at C-8 position have shown promising anticancer activity in various cell lines. The molecules synthesized are of immense biological significance with potential sequence selective DNA-binding property. This resulted in design and synthesis of new congeners as illustrated in Scheme-1, which comprise:

1. The ether linkage at C-8 position of DC-81 intermediates with secondary amine.
2. Refluxing the reaction mixture for 24–48 h.
3. Synthesis of C-8 linked PBD antitumour antibiotic imines.
4. Purification by column chromatography using different solvents like ethylacetate, hexane and methanol.

The following examples are given by way of illustrations and therefore should not be constructed to the present limit of the scope of invention.

EXAMPLE 1

A solution of (2S)-N-[4-(3-bromopropoxy)-5-methoxy-2-nitrobenzoyl]pyrrolidine-2-carboxaldehyde diethyl thioacetal of formula I (521 mg, 1 mmol), 8-hydroxy-7-methoxy-(11aS)-1,2,3,10,11,11a-hexahydro-5H-pyrrolo[2,1-c][1,4]benzodiazepine-5-one (248 mg, 1 mmol) of the formula II and $K_2CO_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc:hexane (8:2) gave the pure (2S)-N-{4-[3-(7-Methoxy-(11aS)-1,2,3,10,11,11a-hexahydro-5H-pyrrolo[2,1-][1,4]benzodiazepine-5-one-8-yloxy)propoxy]-5-methoxy-2-nitrobenzoyl}pyrrolidine-2-carboxaldehyde diethyl thioacetal III.

$^1$H NMR ($CDCl_3$) Γ 1.35–1.45 (m, 6H), 1.70–2.45 (m, 10H), 2.72–2.90 (m, 4H), 3.20–3.28 (m, 3H), 3.50–3.58 (m, 1H), 3.62–3.75 (m, 1H) 3.80–3.90 (m, 4H), 4.20 (t, 2H), 4.35 (t, 2H), 4.65–4.75 (m, 1H), 4.85 (d, 1H, J=4.28 Hz), 6.25 (s, 1H), 6.82 (s, 1H) 7.48 (s, 1H), 7.72 (s, 1H); MS (FAB) 689 $[M+H]^+$.

The (2S)-N-{4-[3-(7-Methoxy-(11aS)-1,2,3,10,11,11a-hexahydro-5H-pyrrolo[2,1-c][1,4]benzodiazepine-5-one-8-yloxy)propoxy]-5-methoxy-2-nitrobenzoyl}pyrrolidine-2-carboxaldehyde diethyl thioacetal III (688 mg, 1.0 mmol) was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude (2S)-N-{4-[3-(7-Methoxy-(11aS)-1,2,3,10,11,11a-hexahydro-5H-pyrrolo[2,1-c][1,4]benzodiazepine-5-one-8-yloxy)propoxy]-5-methoxy-2-aminobenzoyl}pyrrolidine-2-carboxaldehyde diethyl thioacetal IV A solution of the (2S)-N-{4-[3-(7-Methoxy-(11aS)-1,2,3,10,11,11a-hexahydro-5H-pyrrolo[2,1-c][1,4]benzodiazepine-5-one-8-yloxy)propoxy]-5-methoxy-2-aminobenzoyl}pyrrolidine-2-carboxaldehyde diethyl thioacetal IV (658 mg, 1 mmol), $HgCl_2$ (794 mg, 2.93 mmol) and $CaCO_3$ (300 mg, 3 mmol) in $CH_3CN/H_2O$ (4:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethylacetate. The filterate is evaporated in vacuum to get crude 7-Methoxy-8-{3-[7-methoxy-(11aS)-1,2,3,10,11,11a-hexahydro-5H-pyrrolo[2,1-c][1,4]benzodiazepine-5-one-8-yloxy]propoxy}-(11aS)-1,2,3,11a-tetrahydro-5H-pyrrolo[2,1-c][1,4]benzodiazepine-5-one of formula V, which was further purified by column chromatography on silica gel eluting with methanol:EtOAc (2:8).

$^1$H NMR ($CDCl_3$) Γ 1.65–2.45 (m, 10H), 3.15–3.25 (m, 2H), 3.48–3.75 (m, 4H), 3.78–3.88 (m, 4H), 3.90 (s, 3H), 4.25–4.35 (m, 5H), 6.18 (s, 1H), 6.82 (s, 1H), 7.48 (s, 1H), 7.52 (s, 1H), 7.65 (d, 1H, J=4.8 Hz); MS (FAB) 535 $[M+H]^+$.

EXAMPLE 2

A solution of (2S)-N-[4-(4-bromobutoxy)-5-methoxy-2-nitrobenzoyl]pyrrolidine-2-carboxaldehyde diethyl thioacetal of formula I (535 mg, 1 mmol), 8-hydroxy-7-methoxy-(11aS)-1,2,3,10,11,11a-hexahydro-5H-pyrrol[2,1-c][1,4]benzodiazepine-5-one (248 mg, 1 mmol) of the formula II and $K_2CO_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc:hexane (8:2) gave the pure (2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-nitrobenzoyl}pyrrolidine-2-carboxaldehyde diethyl thioacetal III.

$^1$H NMR ($CDCl_3$) Γ 1.35–1.45 (m, 6H), 1.70–2.45 (m, 12H), 2.72–2.90 (m, 4H), 3.20–3.28 (m, 3H), 3.50–3.58 (m, 1H), 3.62–3.75 (m, 1H) 3.80–3.90 (m, 4H), 4.20 (t, 2H), 4.35 (t, 2H), 4.65–4.75 (m, 1H), 4.85 (d, 1H, J=4.28 Hz), 6.25 (s, 1H), 6.82 (s, 1H), 7.48 (s, 1H), 7.72 (s, 1H); MS (FAB) 703 $[M+H]^+$.

The (2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-nitrobenzoyl}pyrrolidine-2-carboxaldehyde diethyl thioacetal (702 mg, 1.0 mmol) of the formula III was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethylacetate (3×20 mL). The combined organic phase was dried over $Na_2SO_4$ and evaporated under vacuum to afford the crude (2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-aminobenzoyl}pyrrolidine-2-carboxaldehyde diethyl thioacetal IV.

A solution of the (2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-aminobenzoyl}pyrrolidine-2-carboxaldehyde diethyl thioacetal of formula IV. (672 mg, 1 mmol), $HgCl_2$ (794 mg, 2.93 mmol) and $CaCO_3$ (300 mg, 3 mmol) in $CH_3CN/H_2O$ (4:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethylacetate. The filterate is evaporated in vacuum to get crude 7-Methoxy-8-{4-[7-methoxy-(11aS)-1,2,3,10,11,11a-hexahydro-5H-pyrrolo[2,1-c][1,4]benzodiazepine-5-one-8-yloxy]butoxy}-(11aS)-1,2,3,11a-tetrahy-dro-5H-pyrrolo[2,1-c][1,4]benzodiazepine-5-one of formula V, which was further purified by column chromatography on silica gel eluting with methanol:EtOAc (2:8).

$^1$H NMR ($CDCl_3$) Γ 1.65–2.45 (m, 10H), 3.15–3.25 (m, 2H), 3.48–3.75 (m, 4H), 3.78–3.88 (m, 4H), 3.90 (s, 3H), 4.25–4.35 (m, 5H), 6.18 (s, 1H), 6.82 (s, 1H), 7.48 (s, 1H), 7.52 (s, 1H), 7.65 (d, 1H, J=4.8 Hz); MS (FAB) 549 [M+H]$^+$.

EXAMPLE 3

A solution of (2S)-N-[4-(5-bromopentyloxy)-5-methoxy-2-nitrobenzoyl]pyrrolidine-2-carboxaldehyde diethyl thioacetal of formula I. (549 mg, 1 mmol), 8-hydroxy-7-methoxy-(11aS)-1,2,3,10,11,11a-hexahydro-5H-pyrrolo[2,1-c][1,4]benzodiazepine-5-one (248 mg, 1 mmol) II and $K_2CO_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc:hexane (8:2) gave the pure (2S)-N-{4-[5-(7-Methoxy-(11aS)-1,2,3,10,11,11a-hexahydro-5H-pyrrolo[2,1-c][1,4]benzodiazepine-5-one-8-yloxy)pentyloxy]-5-methoxy-2-nitrobenzoyl}pyrrolidine-2-carboxaldehyde diethyl thioacetal III.

$^1$H NMR ($CDCl_3$) Γ 1.30–1.40 (m, 6H), 1.65–2.35 (m, 14H), 2.65–2.75 (m, 4H), 3.18–3.32 (m, 3H), 3.45–3.75 (m, 2H), 3.80–3.85 (s 4H), 3.85–4.0 (m, 5H), 4.65–4.72 (m, 1H), 4.85 (d, 1H, J=4.38 Hz), 6.0 (s, 1H), 6.78 (s, 1H) 7.52 (s, 1H), 7.65 (s, 1H); MS (FAB) 717 [M+H]$^+$.

The (2S)-N-{4-[5-(7-Methoxy-(11aS)-1,2,3,10,11,11a-hexahydro-5H-pyrrolo[2,1-c][1,4]-benzodiazepine-5-one-8-yloxy)pentyloxy]-5-methoxy-2-nitrobenzoyl}pyrrolidine-2-carboxaldehyde diethyl thioacetal III (716 mg, 1.0 mmol) was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude (2S)-N-{4-[5-(7-Methoxy-(11aS)-1,2,3,10,11,11a-hexahydro-5H-pyrrolo[2,1-c][1,4]benzodiazepine-5-one-8-yloxy)pentyloxy]-5-methoxy-2-aminobenzoyl]pyrrolidine-2-carboxaldehyde diethyl thioacetal of formula IV.

A solution of (2S)-N-{4-[5-(7-Methoxy-(11aS)-1,2,3,10,11,11a-hexahydro-5H-pyrrolo-[2,1-c][1,4]benzodiazepine-5-one-8-yloxy)pentyloxy]-5-methoxy-2-aminobenzoyl}pyrrolidine-2-carboxaldehyde diethyl thioacetal IV. (686 mg, 1 mmol), $HgCl_2$ (794 mg, 2.93 mmol) and $CaCO_3$ (300 mg, 3 mmol) in $CH_3CN/H_2O$ (4:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered thorough celite and washed with ethylacetate. The filterate is evaporated in vacuum to get crude 7-Methoxy-8-{5-[7-methoxy-(11aS)-1,2,3,10,11,11a-hexahydro-5H-pyrrolo[2,1-c][1,4]benzodiazepine-5-one-8-yloxy]butoxy}-(11as)-1,2,3,11a-tetrahydro-5H-pyrrolo[2,1-c][1,4]benzodiazepine-5-one of formula V, which was further purified by column chromatography on silica gel eluting with methanol:EtOAc (2:8).

$^1$H NMR ($CDCl_3$) Γ 1.20–2.45 (m, 14H), 3.10–3.20 (m, 2H), 3.20–3.28 (m,1H), 3.40–3.78 (m, 5H), 3.80 (s, 3H), 3.98 (s, 3H), 4.10–4.22 (m, 4H), 6.0 (s, 1H), 7.02 (s, 1H); 7.50 (s, 1H), 7.55 (s, 1H), 7.65 (d, 1H, J=5.1 Hz); MS (FAB) 563 [M+H]$^+$.

EXAMPLE 4

A solution of (2S)-N-[4-(3-bromopropoxy)-5-methoxy-2-nitrobenzoyl]pyrrolidine-2-carboxaldehyde diethyl thioacetal of formula I (521 mg, 1 mmol), 8-hydroxy-7-methoxy-(2R)-hydroxy-(11aS)-1,2,3,10,11,11a-hexahydro-5H-pyrrolo[2,1-c][1,4]benzodiazepine-5-one (264 mg, 1 mmol) of the formula II and $K_2CO_3$ (414 mg, 3 mmol) in dry acetone (20 mL) was refluxed for 24–48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (2S)-N-{4-[3-(7-Methoxy-(2R)-hydroxy-(11aS)-1,2,3,10,11,11a-hexahydro-5H-pyrrolo[2,1][1,4]benzodiazepine-5-one-8-yloxy)propoxy]-5-methoxy-2-nitrobenzoyl}pyrrolidine-2-carboxaldehyde diethyl thioacetal III.

The (2S)-N-{4-[3-(7-Methoxy-(2R)-hydroxy-(11aS)-1,2,3,10,11,11a-hexahydro-5H-pyrrolo[2,1-c][1,4]benzodiazepine-5-one-8-yloxy)propoxy]-5-methoxy-2-nitrobenzoyl}pyrrolidine-2-carboxaldehyde diethyl thioacetal III (704 mg, 1.0 mmol) was dissolved in dichloromethane (5 mL), methanol (10 mL) and added $SnCl_2.2H_2O$ (1.124 g, 5.0 mmol), was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude (2S)-N-{4-[3-(7-Methoxy-(2R)-hydroxy-(11aS)-1,2,3,10,11,11a-hexahydro-5H-pyrrolo[2,1-c][1,4]benzodiazepine-5-one-8-yloxy)propoxy]-5-methoxy-2-aminobenzoyl}pyrrolidine-2-carboxaldehyde diethyl thioacetal IV A solution of the (2S)-N-{4-[3-(7-Methoxy-(2R)-hydroxy-(11aS)-1,2,3,10,11,11a-hexahydro-5H-pyrrolo[2, 1-c][1,4]benzodiazepine-5-one-8-yloxy)propoxy]-5-methoxy-2-aminobenzoyl}pyrrolidine-2-carboxaldehyde diethyl thioacetal IV (674 mg, 1 mmol), HgCl$_2$ (794 mg, 2.93 mmol) and CaCO$_3$ (300 mg, 3 mmol) in CH$_3$CN/H$_2$O (4:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethylacetate. The filterate is evaporated in vacuum to get crude 7-Methoxy-8-{3-[7-methoxy-(11aS)-1,2,3,10,11,11a-hexahydro-5H-pyrrolo[2,1-c][1,4]benzodiazepine-5-one-8-yloxy]propoxy}-(11aS)-1,2,3,11a-tetrahydro-5H-pyrrolo[2,1-c][1,4]benzodiazepine-5-one of formula V, which was further purified by column chromatography on silica gel eluting with methanol:EtOAc (3:7).

EXAMPLE 5

A solution of (2S)-N-[4-(4-bromobutoxy)-5-methoxy-2-nitrobenzoyl]pyrrolidine-2-carboxaldehyde diethyl thioacetal of formula I (535 mg, 1 mmol), 8-hydroxy-7-methoxy-(2R)-hydroxy-(11aS)-1,2,3,10,11,11a-hexahydro-5H-pyrrol[2,1-c][1,4]benzodiazepine-5-one (264 mg, 1 mmol) of the formula II and K$_2$CO$_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (2S)-N-{4-[4-(7-methoxy-(2R)-hydroxy-(11aS)-1,2,3,10,11,11a-hexahydro-5H-pyrrolo-[2,1-c][1,4]benzodiazepine-5-one-8-yloxy)butoxy]-5-methoxy-2-nitrobenzoyl}pyrrolidine-2-carboxaldehyde diethyl thioacetal III.

The (2S)-N-{4-[4-(7-methoxy-(2R)-hydroxy-(11aS)-1,2,3,10,11,11a-hexahydro-5H-pyrrolo[2,1-c][1,4]benzodiazepine-5-one-8-yloxy)butoxy]-5-methoxy-2-nitrobenzoyl}pyrrolidine-2-carboxaldehyde diethyl thioacetal (718 mg, 1.0 mmol) of the formula III was dissolved in dichloromethane (5 mL), methanol (10 mL) and added SnCl$_2$.2H$_2$O (1.124 g, 5.0 mmol) was refluxed for 1.5 h. The reaction mixture was then carefully adjusted to pH 8 with saturated NaHCO$_3$ solution and then extracted with ethyl acetate (3×20 mL). The combined organic phase was dried over Na$_2$SO$_4$ and evaporated under vacuum to afford the crude (2S)-N-{4-[4-(7-Methoxy-(2R)-hydroxy-(11aS)-1,2,3,10,11,11a-hexahydro-5H-pyrrolo [2,1-c][1,4] benzodiazepine-5-one-8-yloxy)butoxy]-5-methoxy-2-aminobenzoyl}-pyrrolidine-2-carboxaldehyde diethyl thioacetal IV.

A solution of the (2S)-N-{4-[4-(7-methoxy-(2R)-hydroxy-(11aS)-1,2,3,10,11,11a-hexahydro-5H-pyrrolo[2,1-c][1,4]benzodiazepine-5-one-8-yloxy)butoxy]-5-methoxy-2-aminobenzoyl}pyrrolidine-2-carboxaldehyde diethyl thioacetal of formula IV. (688 mg, 1 mmol), HgCl$_2$ (794 mg, 2.93 mmol) and CaCO$_3$ (300 mg, 3 mmol) in CH$_3$CN/H$_2$O (4:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered through celite and washed with ethylacetate. The filterate is evaporated in vacuum to get crude 7-methoxy-8-{4-[7-methoxy-(2R)-hydroxy-(11aS)-1,2,3,10,11,11a-hexahydro-5H-pyrrolo[2,1-c][1,4]benzodiazepine-5-one-8-yloxy]butoxy}(11aS)-1,2,3,11a-tetrahy-dro-5H-pyrrolo[2,1-c][1,4]benzodiazepine-5-one of formula V, which was further purified by column chromatography on silica gel eluting with methanol:EtOAc (3:7).

EXAMPLE 6

A solution of (2S)-N-[4-(5-bromopentyloxy)-5-methoxy-2-nitrobenzoyl]pyrrolidine-2-carboxaldehyde diethyl thioacetal of formula I. (549 mg, 1 mmol), 8-hydroxy-7-methoxy-(2R)-hydroxy-(11aS)-1,2,3,10,11,11a-hexahydro-5H-pyrrolo[2,1-c][1,4]benzodiazepine-5-one (264 mg, 1 mmol) II and K$_2$CO$_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (2S)-N-{4-[5-(7-Methoxy-(2R)-hydroxy-(11aS)-1,2,3,10,11,11a-hexahydro-5H-pyrrolo-[2,1-c][1,4]benzodiazepine-5-one-8-yloxy)pentyloxy]-5-methoxy-2-nitrobenzoyl}pyrrolidine-2-carboxaldehyde diethyl thioacetate III.

The (2S)-N-{4-[5-(7-Methoxy-(2R)-hydroxy-(11aS)-1,2,3,10,11,11a-hexahydro-5H-pyrrolo[2,1-c][1,4] benzodiazepine-5-one-8-yloxy)pentyloxy]-5-methoxy-2-nitrobenzoyl}pyrrolidine-2-carboxaldehyde diethyl thioacetal III (732 mg, 1.0 mmol) was dissolved in dichloromethane (5 mL), methanol (10 mL) and added SnCl$_2$.2H$_2$O (1.124 g, 5.0 mmol) was refluxed for 1.5 h. The reaction mixture was then carefully adjusted to pH 8 with saturated NaHCO$_3$ solution and then extracted with ethylacetate (3×20 mL). The combined organic phase was dried over Na$_2$SO$_4$ and evaporated under vacuum to afford the crude (2S)-N-{4-[5-(7-Methoxy-(2R)-hydroxy-(11aS)-1,2,3,10,11,11a-hexahydro-5H-pyrrolo[2,1-c][1,4] benzodiazepine-5-one-8-yloxy)pentyloxy]-5-methoxy-2-aminobenzoyl]pyrrolidine-2-carboxaldehyde diethyl thioacetal of formula IV.

A solution of (2S)-N-{4-[5-(7-Methoxy-(2R)-hydroxy-(11aS)-1,2,3,10,11,11a-hexahydro-5H-pyrrolo[2,1-c][1,4] benzodiazepine-5-one-8-yloxy)pentyloxy]-5-methoxy-2-aminobenzoyl}pyrrolidine-2-carboxaldehyde diethyl thioacetal IV. (702 mg, 1 mmol), HgCl$_2$ (794 mg, 2.93 mmol) and CaCO$_3$ (300 mg, 3 mmol) in CH$_3$CN/H$_2$O (4:1, 15 mL) was stirred at room temperature for 12 h until TLC (EtOAc:methanol), indicates complete loss of starting material. Then organic layer is evaporated in vacuum and the residue is diluted with EtOAc. To this saturated NaHCO$_3$ was added slowly at room temperature and the mixture is filtered thorough celite and washed with ethylacetate. The filterate is evaporated in vacuum to get crude 7-Methoxy-8-{5-[7-methoxy-(2R)-hydroxy-(11aS)-1,2,3,10,11,11a-hexahydro-5H-pyrrolo[2,1-c][1,4]benzodiazepine-5-one-8-yloxy]butoxy}(11aS)-1,2,3,11a-tetrahydro-5H-pyrrolo[2,1-c][1,4]benzodiazepine-5-one of formula V, which was further purified by column chromatography on silica gel eluting with methanol:EtOAc (3:7).

EXAMPLE 7

A solution of (4R)-hydroxy-(2S)-N-[4-(3-bromopropoxy)-5-methoxy-2-nitrobenzoyl]-pyrrolidine-2-carboxaldehyde diethyl thioacetal of formula I (537 mg, 1 mmol), 8-hydroxy-7-methoxy-(11aS)-1,2,3,10,11,11a-hexahydro-5H-pyrrolo[2,1-c][1,4]benzodiazepine-5-one (248 mg, 1 mmol) of the formula II and K$_2$CO$_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (4R)-hydroxy-(2S)-N-{4-[3-(7-Methoxy-(11aS)-1,2,3,10,11,11a-hexahydro-5H-pyrrolo[2,1-c][1,4] benzodiazepine-5-one-8-yloxy)propoxy]-5-methoxy-2-nitrobenzoyl}pyrrolidine-2-carboxaldehyde diethyl thioacetal III.

The (4R)-hydroxy-(2S)-N-{4-[3-(7-Methoxy-(11aS)-1,2,3,10,11,11a-hexahydro-5H-pyrrolo[2,1-c][1,4] benzodiazepine-5-one-8-yloxy)propoxy]-5-methoxy-2-nitrobenzoyl}pyrrolidine-2-carboxaldehyde diethyl thioacetal III (704 mg, 1.0 mmol) was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude (2S)-N-{4-[3-(7-Methoxy-(11aS)-1,2,3,10,11,11a-hexahydro-5H-pyrrolo[2,1-c][1,4]benzodiazepine-5-one-8-yloxy)propoxy]-5-methoxy-2-aminobenzoyl}pyrrolidine-2-carboxaldehyde diethyl thioacetal IV A solution of the (4R)-hydroxy-(2S)-N-{4-[3-(7-Methoxy-(11aS)-1,2,3,10,11,11a-hexahydro-5H-pyrrolo[2,1-c][1,4]benzodiazepine-5-one-8-yloxy)propoxy]-5-methoxy-2-aminobenzoyl}pyrrolidine-2-carboxaldehyde diethyl thioacetal IV (674 mg, 1 mmol), $HgCl_2$ (794 mg, 2.93 mmol) and $CaCO_3$ (300 mg, 3 mmol) in $CH_3CN/H_2O$ (4:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethylacetate. The filterate is evaporated in vacuum to get crude 7-Methoxy-8-{3-[7-methoxy-(11aS)-1,2,3,10,11,11a-hexahydro-5H-pyrrolo[2,1-c][1,4]benzodiazepine-5-one-8-yloxy]propoxy}-(4R)-hydroxy-(11aS)-1,2,3,11a-tetrahydro-5H-pyrrolo[2,1-c][1,4]benzodiazepine-5-one of formula V, which was further purified by column chromatography on silica gel eluting with methanol:EtOAc (3:7).

EXAMPLE 8

A solution of (4R)-hydroxy-(2S)-N-[4-(4-bromobutoxy)-5-methoxy-2-nitrobenzoyl]Pyrrolidine-2-carboxaldehyde diethyl thioacetal of formula I (551 mg, 1 mmol), 8-hydroxy-7-methoxy-(11aS)-1,2,3,10,11,11a-hexahydro-5H-pyrrol[2,1-c][1,4]benzodiazepine-5-one (248 mg, 1 mmol) of the formula II and $K_2CO_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (4R)-hydroxy-(2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-nitrobenzoyl}pyrrolidine-2-carboxaldehyde diethyl thioacetal III.

The (4R)-hydroxy-(2S)-N-{4-[4-(7-Methoxy-(11aS)-1,2,3,10,11,11a-hexahydro-5H-pyrrolo[2,1-c][1,4] benzodiazepine-5-one-8-yloxy)butoxy]-5-methoxy-2-nitrobenzoyl}pyrrolidine-2-carboxaldehyde diethyl thioacetal (718 mg, 1.0 mmol) of the formula III was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethylacetate (3×20 mL). The combined organic phase was dried over $Na_2SO_4$ and evaporated under vacuum to afford the crude (2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-aminobenzoyl}pyrrolidine-2-carboxaldehyde diethyl thioacetal IV.

A solution of the (4R)-hydroxy-(2S)-N-{4-[4-(7-Methoxy-(11aS)-1,2,3,10,11,11a-hexahydro-5H-pyrrolo[2,1-c][1,4]benzodiazepine-5-one-8-yloxy)butoxy]-5-methoxy-2-aminobenzoyl}pyrrolidine-2-carboxaldehyde diethyl thioacetal of formula IV. (688 mg, 1 mmol), $HgCl_2$ (794 mg, 2.93 mmol) and $CaCO_3$ (300 mg, 3 mmol) in $CH_3CN/H_2O$ (4:1, 15 mL) was stirred at room temperature for 12 h until TLC (EtOAc), indicates complete loss of starting material. Then organic layer is evaporated in vacuum and the residue is diluted with EtOAc. To this saturated $NaHCO_3$ was added slowly at room temperature and the mixture is filtered through celite and washed with ethylacetate. The filterate is evaporated in vacuum to get crude 7-Methoxy-8-{4-[7-methoxy-(11aS)-1,2,3,10,11,11a-hexahydro-5H-pyrrolo[2,1-c][1,4]benzodiazepine-5-one-8-yloxy]butoxy}-(4R)-hydroxy-(11aS)-1,2,3,11a-tetrahydro-5H-pyrrolo[2,1-c][1,4]benzodiazepine-5-one of formula V, which was further purified by column chromatography on silica gel eluting with methanol:EtOAc (2:8).

EXAMPLE 9

A solution of (4R)-hydroxy-(2S)-N-[4-(5-bromopentyloxy)-5-methoxy-2-nitrobenzoyl]-pyrrolidine-2-carboxaldehyde diethyl thioacetal of formula I. (565 mg, 1 mmol), 8-hydroxy-7-methoxy-(11aS)-1,2,3,10,11,11a-hexahydro-5H-pyrrolo[2,1-c][1,4]benzodiazepine-5-one (248 mg, 1 mmol) II and $K_2CO_3$ (414 mg, 3 mmol) in dry acetone (20 mL) was refluxed for 48 h. After the completion of reaction as indicated by TLC, EtOAc, the reaction mixture was poured on to the water and then extracted with ethylacetate. Evaporation of the organic layer gave the crude product, which was further purified by column chromatography on silica gel eluting with EtOAc gave the pure (4R)-hydroxy-(2S)-N-{4-[5-(7-Methoxy-(11aS)-1,2,3,10,11,11a-hexahydro-5H-pyrrolo[2,1-c][1,4]benzodiazepine-5-one-8-yloxy)pentyloxy]-5-methoxy-2-nitrobenzoyl}pyrrolidine-2-carboxaldehyde diethyl thioacetal III.

The (4R)-hydroxy-(2S)-N-{4-[5-(7-Methoxy-(11aS)-1,2,3,10,11,11a-hexahydro-5H-pyrrolo[2,1-c][1,4] benzodiazepine-5-one-8-yloxy)pentyloxy]-5-methoxy-2-nitrobenzoyl}pyrrolidine-2-carboxaldehyde diethyl thioacetal III (732 mg, 1.0 mmol) was dissolved in dichloromethane (5 mL), methanol (10 mL) and added $SnCl_2.2H_2O$ (1.124 g, 5.0 mmol) was refluxed for 1.5 h. The reaction mixture was then carefully adjusted to pH 8 with saturated $NaHCO_3$ solution and then extracted with ethyl acetate (3×20 mL). The combined organic phase was dried over $Na_2SO_4$ and evaporated under vacuum to afford the crude (4R)-hydroxy-(2S)-N-{4-[5-(7-Methoxy-(11aS)-1,2,3,10,11,111a-hexahydro-5H-pyrrolo[2,1-c][1,4] benzodiazepine-5-one-8-yloxy)pentyloxy]-5-methoxy-2-aminobenzoyl]pyrrolidine-2-carboxaldehyde diethyl thioacetal of formula IV.

A solution of (4R)-hydroxy-(2S)-N-{4-[5-(7-Methoxy-(11as)-1,2,3,10,11,11a-hexahydro-5H-pyrrolo[2,1-c][1,4]

benzodiazepine-5-one-8-yloxy)pentyloxy]-5-methoxy-2-aminobenzoyl}pyrrolidine-2-carboxaldehyde diethyl thioacetal IV. (702 mg, 1 mmol), HgCl$_2$ (794 mg, 2.93 mmol) and CaCO$_3$ (300 mg, 3 mmol) in CH$_3$CN/H$_2$O (4:1, 15 mL) was stirred at room temperature for 12 h until TLC (EtOAc), indicates complete loss of starting material. Then organic layer is evaporated in vacuum and the residue is diluted with EtOAc. To this saturated NaHCO$_3$ was added slowly at room temperature and the mixture is filtered thorough celite and washed with ethylacetate. The filtrate is evaporated in vacuum to get crude 7-Methoxy-8-{5-[7-methoxy-(11aS)-1,2,3,10,11,11a-hexahydro-5H-pyrrolo[2,1-c][1,4]benzodiazepine-5-one-8-yloxy]butoxy}-(4R)-hydroxy-(11aS)-1,2,3,11a-tetrahydro-5H-pyrrolo[2,1-c][1,4]benzodiazepine-5-one of formula V, which was further purified by column chromatography on silica gel eluting with methanol:EtOAc (2:8).

Biological Activity. In vitro biological activity studies were carried out at National Cancer Institute (USA).

Cytotoxicity. Compounds Va and Vc were evaluated in vitro against sixty human tumour cells derived from nine cancer types (leukemia, non-small-cell lung, colon, CNS, melanoma, ovarian, prostate, and breast cancer). For each compound, dose response curves for each cell line were measured at a minimum of five concentrations at 10 fold dilutions. A protocol of 48 h continuous drug exposure was used, and a sulforhodamine B (SRB) protein assay was used to estimate cell viability or growth. The concentration causing 50% cell growth inhibition (GI50), total cell growth inhibition (TGI 0% growth) and 50% cell death (LC50, −50% growth) compared with the control was calculated. The mean graph midpoint values of log$_{10}$TGI and log$_{10}$LC50 as well as log$_{10}$ GI50 for Va and Vc are listed in Table 1. As demonstrated by mean graph pattern, compound VIc exhibits an interesting profile of activity and selectivity for various cell lines. The mean graph mid point of log$_{10}$ TG1 and log$_{10}$ LC50 showed similar pattern to the log$_{10}$ GI50 mean graph mid points.

TABLE 1 log$_{10}$ GI50 log$_{10}$ TGI and log$_{10}$ LC50 mean graphs midpoints (MG_MID) of in vitro Cytotoxicity data for the compounds Va and Vc against human tumor cell lines.

| Compound | Log$_{10}$ GI50 | Log$_{10}$ TGI | Log$_{10}$ LC50 |
|---|---|---|---|
| Va | −6.80 | −5.73 | −4.48 |
| Vc | −5.29 | −4.55 | −4.15 |

TABLE 2

Log LC50 (concentration in mol/L causing 50% lethality) Values for Compounds Va and Vc

| Cancer | Compound Va | Compound Vc |
|---|---|---|
| leukemia | −4.08 | −4.46 |
| non-small-cell lung | −4.41 | −4.14 |
| colon | −4.59 | −4.04 |
| CNS | −4.49 | −4.09 |
| melanoma | −5.45 | −4.42 |
| ovarian | −4.15 | −4.01 |
| renal | −4.20 | −4.02 |
| prostate | −4.08 | −4.00 |
| Breast | −4.36 | −4.05 |

Each cancer type represents the average of six to eight different cancer cell lines.

The anticancer activity for two representative compounds has been given in Table 2. The comparison of the data of Table 2 reveals the importance of the alkane spacer. As the alkane spacer increased from 3–5 the cytotoxic activity has moderately decreased. The 3 carbon spacer of compound Va confers a suitable fit in the minor groove of double helix DNA and shows slightly higher activity in this series of compounds Va and Vc.

What is claimed is:

1. A compound of the formula (V), in which R and R$_1$ are independently H or —OH, and n is an integer from 3 to 5.

2. The compound of claim 1, in which R=R$_1$=H and n=3.
3. The compound of claim 1, in which R=R$_1$=H and n=4.
4. The compound of claim 1, in which R=R$_1$=H and n=5.
5. The compound of claim 1, in which R=H, R$_1$=OH and n=3.
6. The compound of claim 1, in which R=H, R$_1$=OH and n=4.
7. The compound of claim 1, in which R=H, R$_1$=OH and n=5.
8. The compound of claim 1, in which R=OH, R$_1$=H and n=3.
9. The compound of claim 1, in which R=OH, R$_1$=H and n=4.
10. The compound of claim 1, in which R=OH, R$_1$=H and n=5.
11. A process for preparing a compound of the formula (V)

a) reacting a compound of the formula (I) with a compound of the formula (II) in presence of a mild base in a water miscible aprotic organic solvent and refluxing for a period of 16 h to 48 h, b) pouring the reaction mixture of step (a) into water, extracting with ethyl acetate and separating the organic layer, c) evaporating the organic layer of step (b) to obtain a residue which is purified to obtain a compound of formula (III),

III d) reducing the compound of formula (III) in a halogenated solvent, adding stannous chloride dehydrate, and refluxing for a period of 0.5 h to 2 h,
e) adjusting the pH of the reaction mixture of step (d) to 8.0 using an alkali bicarbonate solution,
f) extracting the PH-adjusted mixture of (e) with ethylacetate, evaporating the ethylacetate extract under reduced pressure to obtain a crude compound of formula (IV),

IV g) providing a solution of compound of formula (IV) in a mixture of acetonitrile/$H_2O$, adding mercuric chloride and calcium carbonate, and stirring at room temperature for 6 h to 12 h,

IV h) filtering and evaporating the organic layer under reduced pressure to obtain a residue which is then diluted with ethyl acetate,
i) adding a saturated solution of sodium bicarbonate to the ethylacetate solution of step (h) at room temperature,
j) filtering the solution of step (i) through a celite bed, evaporating the filtrate to obtain a residue containing crude compound of formula V, and

V $R = R_1 = H, OH$
$n = 3–5$ k) purifying the crude compound of step (j) using silica gel as an adsorbent to obtain a pure compound of formula (V); wherein R and $R_1$ where R and $R_1$ is H and/or OH; and n is 3 to 5.

12. The process of claim 11, wherein in step (a) the aprotic organic solvent used is selected from the group consisting of tetrahydrofuran, acetone and dimethyl formamide.

13. The process of claim 11, wherein in step (a) the mild base used is selected from the group consisting of sodium carbonate, potassium carbonate, lithium carbonate, barium carbonate and cesium carbonate.

14. The process of claim 11, wherein in step (d) the halogenated solvent used is selected from the group consisting of carbon tetrachloride, chloroform and dichloromethane.

15. The process of claim 14, wherein the solvent used is dichloromethane.

16. The process of claim 11, wherein in step (c) the alkali carbonate solution used is a solution of sodium bicarbonate potassium bicarbonate or lithium bicarbonate.

17. A pharmaceutical composition comprising an effective amount of the compound of claim 1 and a pharmaceutically acceptable carrier.

18. A method for inhibiting tumor growth or treating a cancer in a subject, the tumor or cancer being one selected from the group consisting of leukemia, non-small cell lung carcinoma, colon cancer, a central nervous system tumor, melanoma, ovarian cancer, prostate cancer and breast cancer, comprising administering the compound of claim 1 to the subject.

* * * * *